United States Patent [19]

Hyoda et al.

[11] Patent Number: 6,040,453
[45] Date of Patent: Mar. 21, 2000

[54] METHOD FOR PREPARING 5,5'-BI-1H-TETRAZOLE SALT

[75] Inventors: Shunji Hyoda; Masaharu Kita; Hirotoshi Sawada; Shuichi Nemugaki, all of Sakaide; Sumio Otsuka, Takamatsu; Yoshitaka Miyawaki, Takamatsu; Takashi Ogawa, Takamatsu; Yuhki Kubo, Takamatsu, all of Japan

[73] Assignees: Japan Hydrazine Co., Inc; Masuda Chemical Industry Co., Ltd., both of Japan

[21] Appl. No.: 09/374,950

[22] Filed: Aug. 16, 1999

[51] Int. Cl.[7] .................. C07D 257/04; C07D 403/04
[52] U.S. Cl. ............................................. 548/250
[58] Field of Search .............................. 548/250

[56] References Cited

U.S. PATENT DOCUMENTS 2,710,297  6/1955  Friederich ................. 260/308

*Primary Examiner*—Johann Richter
*Assistant Examiner*—Jane C. Osweckí
*Attorney, Agent, or Firm*—Fulbright & Jaworski L.L.P.

[57] ABSTRACT

A process for the preparation of a 5,5'-bi-1H-tetrazole diammonium salt by using dicyan, sodium azide, ammonium chloride and water as a reaction medium. This process is industrially advantageous since the 5,5'-bi-1H-tetrazole diammonium salt is synthesized and, then, the precipitated crystals thereof are simply isolated by filtration to obtain the 5,5'-bi-1H-tetrazole diammonium salt maintaining an yield which is not lower than 90%. The 5,5'-bi-1H-tetrazole diammonium salt is a gas-generating agent for air bags, which is lowly toxic and is easy to handle.

4 Claims, No Drawings

METHOD FOR PREPARING 5,5'-BI-1H-TETRAZOLE SALT

BACKGROUND OF THE INVENTION

1. Field of the Invention

The present invention relates to a method for preparing a 5,5'-bi-1H-tetrazole diammonium salt that is useful as a lowly toxic and easy-to-handle gas-generating agent for air bags and as a high molecular foaming agent.

2. Description of the Prior Art

A 5,5'-bi-1H-tetrazole (BHT) and its salts have a chemical structure represented by the following formula

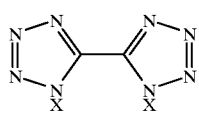
(1)

wherein X is a hydrogen atom or a pair of cations.

There have been known the following four methods of synthesis.

Prior Art 1, Chemical Abstracts Vol. 31, 4985

This literature teaches the synthesis of BHT by the reaction expressed by the following formula (2),

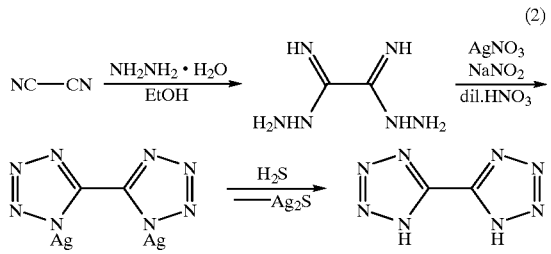
(2)

Prior Art 2, Friederich DE 952,811, 1956

This literature discloses a method for the preparation of a bistetrazole by reacting a mole of sodium azide or hydrogen azide with 2 moles of sodium cyanide or hydrogen cyanide in the presence of a small amount of copper salt, and teaches, in the working examples, the recovery of the bistetrazole (BHT) in the form of a bisodium salt (BHT.2Na) by condensing the solution after the reaction.

This reaction is expressed by the following formula (3),

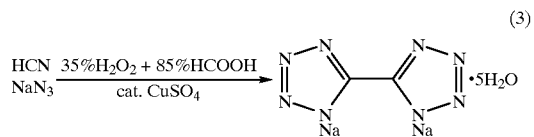
(3)

Prior Art 3, Friederich DE 952,811, 1956, U.S. Pat. No. 2,710,297, 1955

This is the same literature as the one quoted above, and teaches the synthesis of the BHT.2Na by the reaction in accordance with the following formula (4),

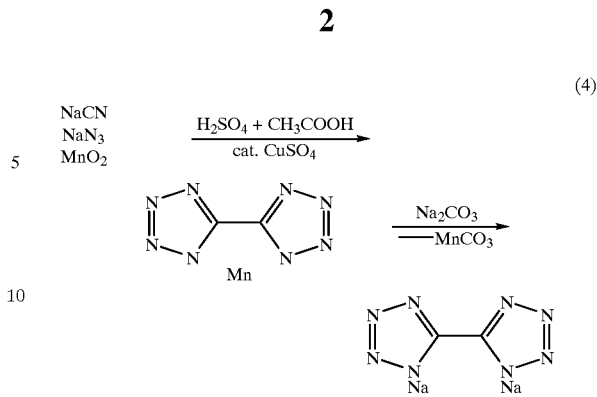
(4)

Prior Art 4, F. Einberg, J. Org. Chem., 29, (1954) 2021

This literature discloses the synthesis of a 5,5'-bi-1H-tetrazole diammonium salt (BHT.2NH$_3$) by the reaction expressed by the following formula (5),

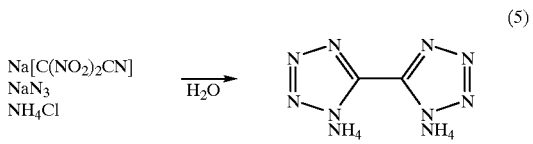
(5)

The prior art 1 teaches the process for obtaining the 5,5'-bi-1H-tetrazole by separating a 5,5'-bi-1H-tetrazole silver salt through the step of forming an azide of an oxalic acid dihydrazide which is a reaction product of a dicyan and a hydrated hydrazine, reacting the 5,5'-bi-1H-tetrazole silver salt with hydrogen sulfide to move it in the form of a silver sulfide. However, this process involves complex steps and requires the use of expensive silver salt and hydrogen sulfide which is toxic.

The prior art 2 teaches the process for synthesizing and isolating the 5,5'-bi-1H-tetrazole disodium salt by using hydrogen cyanide and sodium azide as starting materials. Since the 5,5'-bi-1H-tetrazole disodium salt is soluble in water, it becomes necessary to conduct the step of after-treatment such as condensation for isolating the 5,5'-bi-1H-tetrazole disodium salt from an aqueous solution thereof. Though there has been described that the 5,5'-bi-1H-tetrazole disodium salt is isolated from the aqueous solution through the after-treatment such as condensation, there is no description related to the yields and properties of the isolated compound. The present inventors have conducted trace experiment of Examples of the prior art 2 to find that the yield was as very low as about 30%.

The prior art 3 synthesizes the 5,5'-bi-1H-tetrazole disodium salt by using sodium cyanide, sodium azide and manganese dioxide as an oxidizing agent. However, use of manganese dioxide as an oxidizing agent requires cumbersome after-treatment for removing manganese dioxide.

The prior art 4 uses sodium dinitroacetonitrile, sodium azide and ammonium chloride as starting materials to isolate the 5,5'-bi-1H-tetrazole diammonium salt. However, the reaction time is long, the yield is low and, besides, the sodium dinitroacetonitrile which is the starting material is not easily available.

When the sodium cyanide or hydrogen cyanide is used as a starting material, furthermore, an oxidizing agent is necessary. When a metal salt is used as the oxidizing agent, the reaction intermediate product, i.e., 5,5'-bi-1H-tetrazole metal salt is isolated from the reaction solution and is decomposed arousing, however, a problem of lengthy and complex reaction operation. Besides, use of a heavy metal in the reaction system requires the after-treatment for its removal, which is a serious problem.

In this sense, the method which uses hydrogen peroxide as an oxidizing agent is advantageous but still offers a low yield due to the side reaction of cyan and leaves much room for improvement.

In order to isolate the 5,5'-bi-1H-tetrazole or the 5,5'-bi-1H-tetrazole disodium salt soluble in water, furthermore, the operation such as condensation is required, causing an increase in the number of the steps. Besides, the yield is not satisfactory.

OBJECTS AND SUMMARY OF THE INVENTION

The object of the present invention therefore is to provide an industrially and economically advantageous process for the preparation of a 5,5'-bi-1H-tetrazole diammonium salt maintaining a high purity and a high yield of not lower than 90% by using the inexpensive and easy-to-handle starting materials through a very simple operation of synthesizing the 5,5'-bi-1H-tetrazole diammonium salt and, after the reaction, separating it by filtration.

According to the present invention, there is provided a process for the preparation of a 5,5'-bi-1H-tetrazole diammonium salt by reacting dicyan, sodium azide and ammonium chloride in an aqueous medium.

According to the present invention, in particular, dicyan is added to an aqueous solution containing sodium azide and ammonium chloride under a low-temperature condition and, then, the mixture is reacted by heating to recover the 5,5'-bi-1H-tetrazole diammonium salt in the form of sparingly soluble crystals in a highly pure form maintaining a high yield with respect to the dicyan.

DETAILED DESCRIPTION OF THE PREFERRED EMBODIMENT

According to the present invention, dicyan, sodium azide and ammonium chloride are used in combination as starting materials to obtain a 5,5'-bi-1H-tetrazole diammonium salt in a highly pure form and in a high yield.

In particular, the dicyan is added to an aqueous solution containing sodium azide and ammonium chloride under a low-temperature condition and, then, the mixture is heated so that the dicyan is converted into a 5,5'-bi-1H-tetrazole diammonium salt in a high yield and a high selectivity, the 5,5'-bi-1H-tetrazole diammonium salt being precipitated in the form of sparingly soluble crystals. Therefore, the 5,5'-bi-1H-tetrazole diammonium salt is obtained in a high yield and in a highly pure form through a very simple of operation, i.e., filtration and separation.

The process of the present invention is excellent in regard to that the 5,5'-bi-1H-tetrazole diammonium salt is obtained through a very simple operation maintaining a high yield of not lower than 90% as will be described later by way of working examples.

According to the present invention, it is considered that equal moles of dicyan reacts with equal moles of sodium azide and ammonium chloride or with ammonium azide to form a 5-cyano-1H-tetrazole which is an intermediate product of a 5,5'-bi-1H-tetrazole. Then, this intermediate product reacts with another mole of sodium azide and ammonium chloride or with ammonium azide to form the desired 5,5'-bi-1H-tetrazole diammonium salt.

The dicyan may be added in the form of either a gas or a liquid to the aqueous solution containing sodium azide and ammonium chloride. It is desired that the dicyan is added at a low temperature which is not higher than 10° C. and, particularly, from 0 to 5° C. The dicyan, sodium azide and ammonium chloride are fed at such molar ratios as sodium azide/dicyan=4.0 to 2.0 and, particularly preferably, 2.1 to 3.0, and sodium azide/ammonium chloride=0.9 to 1.5.

The dicyan used for the reaction may be the one synthesized by a method known per se. For example, the liquid dicyan separately synthesized from sodium cyanide/copper sulfate, or the gaseous dicyan generated by the methods disclosed in Japanese Unexamined Patent Publications (Kokai) Nos. 7565/1971 and 38900/1971 may be directly introduced into an aqueous solution containing sodium azide/ammonium chloride to synthesize the 5,5'-bi-1H-tetrazole diammonium salt. Or, the sodium azide and ammonium chloride may be the industrially manufactured products.

After the dicyan is added, the reaction temperature is raised to 45 to 55° C. to conduct the reaction by heating for 0.5 to 2 hours and, particularly preferably, for about one hour to synthesize a 5-cyano-1H-tetrazole which is an intermediate product of the 5,5'-bi-1H-tetrazole. Thereafter, the reaction temperature is raised to 85 to 95° C. to conduct the reaction for 3 to 8 hours and, particularly preferably, for 5 to 7 hours, so that white crystals of the 5,5'-bi-1H-tetrazole diammonium salt which is the object product are gradually precipitated. The progress of reaction can be traced by the liquid chromatography. First, the 5-cyano-1H-tetrazole intermediate product is formed and, then, this intermediate product is gradually converted into the 5,5'-bi-1H-tetrazole diammonium salt. The reaction is continued until the amount of the 5-cyano-1H-tetrazole intermediate product in the reaction solution decreases down to about 1 to 2%.

After the reaction, the reaction solution is cooled down to room temperature, and the precipitated white crystals are separated by filtration to obtain the 5,5'-bi-1H-tetrazole diammonium salt in a high yield of not lower than 90% maintaining a purity of not lower than 98% (liquid chromatography). According to the present invention, the 5,5'-bi-1H-tetrazole diammonium salt is efficiently separated and does not almost remain in the mother liquor of after the separation.

EXAMPLES

The invention will now be concretely described by way of Examples to which only, however, the invention is in no way limited.

The 5,5'-bi-1H-tetrazole, 5-cyano-1H-tetrazole intermediate product and hydrogen azide were analyzed relying on the high performance liquid chromatography, and hydrogen cyanide and dicyan were analyzed relying on the gas chromatography.

The content (purity) of the 5,5'-bi-1H-tetrazole diammonium salt which is the object product in the crystals obtained in Examples was found relying on the $HClO_4$ titration (%) and the high performance liquid chromatography (HPLC area %).

Example 1

An mixed aqueous solution containing 27.2 g (1.002 moles) of 99.66% hydrogen cyanide, 56.3 g (0.503 mole) of 30.49% hydrogen peroxide and 27.2 g of water was cooled to −10° C. and was dropwisely added to a mixed aqueous solution obtained by dissolving 25.1 g (0.100 mole) of a 99.5% pentahydrate of copper sulfate (II) and 25.5 g (0.050 mole) of a 78.3% iron sulfate (III) in 100.0 g of water, at a reaction temperature of from 20 to 25° C. over a period of 3 hours. After the dropwise addition, the mixed solution was ripened at 40° C. for 1 hour to obtain a solution of synthesized dicyan.

A mixed solution obtained by dissolving 65.27 g (1.002 moles) of 99.8% sodium azide and 54.14 g (1.002 moles) of 99.0% of ammonium chloride in 300.0 g of water was cooled to 3 to 5° C., and gaseous dicyan generated from the solution of synthesized dicyan was introduced into the mixed solution over a period of 5 hours. After the introduction of the dicyan gas, the weight of the mixed aqueous solution has increased by 11.71 g [dicyan (0.225 mole)].

The temperature of the reaction solution was raised and the reaction solution was reacted at 50° C. for one hour as a first step to chiefly form a 5-cyano-1H-tetrazole intermediate product. Then, as a second step, the reaction solution was reacted at 90° C. for 4 hours to convert the 5-cyano-1H-tetrazole intermediate product into a 5,5'-bi-1H-tetrazole.

The reaction was traced by using the high performance liquid chromatography. After the reaction, the deaeration was effected under a reduced pressure (200 mmHg) at 60° C. to remove hydrogen azide. Thus, the unreacted and dissolved hydrogen azide was removed. Thereafter, the reaction solution was cooled, and the precipitated white crystals were filtered and washed with 100.0 g of cold water to isolate 45.32 g of wet crystals. After dried at 50° C. under a reduced pressure, there were obtained 36.40 g (0.209 mole) of white needle crystals of the 5,5'-bi-1H-tetrazole diammonium salt maintaining an yield of 93.1% [based on dicyan]. There remained 0.24% by weight or 1.13 g (0.007 mole) of the 5,5'-bi-1H-tetrazole diammonium salt in 471.87 g of the isolated mother liquor.

Analysis of white crystals of 5,5'-bi-1H-tetrazole diammonium salt:

Content:
  HClO$_4$ titration: 99.05%
  HPLC area %: 98.95%

Example 2

An mixed aqueous solution containing 27.0 g (0.995 mole) of 99.66% hydrogen cyanide, 56.3 g (0.503 mole) of water of 30.49% hydrogen peroxide and 27.3 g of water was cooled to −10° C. and was dropwisely added to a mixed aqueous solution obtained by dissolving 25.1 g (0.100 mole) of a 99.5% pentahydrate of copper sulfate (II) and 25.5 g (0.050 mole) of a 78.3% iron sulfate (III) in 100.0 g of water, at a reaction temperature of from 20 to 25° C. over a period of 5.5 hours. After the dropwise addition, the mixed solution was ripened at 40° C. for 1 hour to obtain a solution of synthesized dicyan.

Next, a mixed solution obtained by dissolving 65.27 g (1.002 moles) of 99.8% sodium azide and 54.14 g (1.002 moles) of 99.0% of ammonium chloride in 600.0 g of water was cooled to 2 to 4° C., and gaseous dicyan generated from the solution of synthesized dicyan was introduced into the mixed solution over a period of 5 hours. After the introduction of the dicyan gas, the weight of the mixed aqueous solution has increased by 10.29 g [dicyan (0.210 mole)].

The temperature of the reaction solution was raised and the reaction solution was reacted at 50° C. for one hour as a first step to chiefly form a 5-cyano-1H-tetrazole intermediate product. Then, as a second step, the reaction solution was reacted at 90° C. for 5.5 hours to convert the 5-cyano-1H-tetrazole intermediate product into a 5,5'-bi-1H-tetrazole. After the reaction, the deaeration was effected under a reduced pressure (200 mmHg) at 60° C. to remove hydrogen azide. Thus, the unreacted and dissolved hydrogen azide was removed. Thereafter, the reaction solution was cooled, and the precipitated white crystals were filtered and washed with 100.0 g of cold water to isolate 38.43 g of wet crystals. After dried at 50° C. under a reduced pressure, there were obtained 34.97 g (0.203 mole) of white needle crystals of the 5,5'-bi-1H-tetrazole diammonium salt maintaining an yield of 95.1% [based on dicyan].

There remained 0.10% by weight or 0.81 g (0.005 mole) of the 5,5'-bi-1H-tetrazole diammonium salt in 783.85 g of the isolated mother liquor.

Analysis of white crystals of 5,5'-bi-1H-tetrazole diammonium salt:

Content:
  HClO$_4$ titration: 98.30%
  HPLC area %: 99.80%

Example 3

The separately synthesized dicyan was once collected in a pressure-resistant glass container. Next, 13.04 g (0.250 mole) of the dicyan gas cooled at −20 to −14° C. was introduced into a mixed aqueous solution obtained by dissolving 32.57 g (0.500 mole) of 99.8% sodium azide and 27.02 g (0.500 mole) of 99.0% ammonium chloride in 200.22 g of water at a temperature of from 2.8 to 4° C. over a period of 4 hours.

After the introduction of the dicyan gas, the temperature of the reaction solution was raised to effect the reaction at 50° C. for one hour as a first step to chiefly form a 5-cyano-1H-tetrazole intermediate product. Then, as a second step, the reaction solution was reacted at 90° C. for 6 hours to convert the 5-cyano-1H-tetrazole intermediate product into a 5,5'-bi-1H-tetrazole. After the reaction, the reaction solution was cooled, and the precipitated white crystals were filtered and washed with 100.0 g of cold water to isolate 46.58 g of wet crystals. After dried at 50° C. under a reduced pressure, there were obtained 34.76 g (0.197 mole) of white needle primary crystals of the 5,5'-bi-1H-tetrazole diammonium salt maintaining an yield of 79.0% [based on dicyan].

Furthermore, 6.52 g (0.100 mole) of 99.8% sodium azide and 5.40 g (0.100 mole) of 99.0% ammonium chloride were added to 300.0 g of the isolated mother liquor in which the 5-cyano-1H-tetrazole intermediate product is still remaining, and the mixture was reacted again at 90° C. for 6 hours to convert the remaining 5-cyano-1H-tetrazole intermediate product into the 5,5'-bi-1H-tetrazole. After the reaction, the deaeration was effected under a reduced pressure (200 mmHg) at 60° C. to remove hydrogen azide. Thus, the unreacted and dissolved hydrogen azide was removed. Thereafter, the reaction solution was cooled, and the precipitated white crystals were filtered and washed with 15.2 g of cold water to isolate 6.45 g of wet crystals. After dried at 50° C. under a reduced pressure, there were obtained 5.10 g (0.029 mole) of white needle secondary crystals of the 5,5'-bi-1H-tetrazole diammonium salt maintaining an yield of 11.6% [based on dicyan]. The total yield was 90.6%.

Analysis of white crystals of 5,5'-bi-1H-tetrazole diammonium salt:

| Content: | Primary crystals | HClO$_4$ titration: 97.76% |
| | | HPLC area %: 99.51% |
| | Secondary crystals | HClO$_4$ titration: 98.09% |
| | | HPLC area %: 100.00% |

Example 4

The separately synthesized dicyan was once collected in a pressure-resistant glass container. Next, 12.12 g (0.239 mole) of the dicyan gas cooled at −20 to −14° C. was introduced into a mixed aqueous solution obtained by dissolving 42.36 g (0.650 mole) of 99.8% sodium azide and 35.14 g (0.650 mole) of 99.0% ammonium chloride in 260.13 g of water at a temperature of from 1.2 to 2.3° C. over a period of 5 hours.

After the introduction of the dicyan gas, the temperature of the reaction solution was raised and the reaction was conducted at 50° C. for one hour as a first step to chiefly form a 5-cyano-1H-tetrazole intermediate product. Then, as a second step, the reaction solution was reacted at 90° C. for 6 hours to convert the 5-cyano-1H-tetrazole intermediate product into a 5,5'-bi-1H-tetrazole. After the reaction, the reaction solution was cooled, and the precipitated white crystals were filtered and washed with 103.1 g of cold water to isolate 51.78 g of wet crystals. After dried at 50° C. under a reduced pressure, there were obtained 38.29 g (0.218 mole) of white needle crystals of the 5,5'-bi-1H-tetrazole diammonium salt maintaining an yield of 91.0% [based on dicyan].

Analysis of white crystals of 5,5'-bi-1H-tetrazole diammonium salt:

Content:
   HClO$_4$ titration: 97.79%
   HPLC area %: 99.51%

What is claimed is:

1. A process for the preparation of a 5,5'-bi-1H-tetrazole diammonium salt by reacting dicyan, sodium azide and ammonium chloride in an aqueous medium.

2. A process for the preparation of a 5,5'-bi-1H-tetrazole diammonium salt according to claim 1, wherein the dicyan is introduced into the mixed solution of sodium azide and ammonium chloride under a cooled condition to synthesize and isolate a 5,5'-bi-1H-tetrazole diammonium salt of a high quality maintaining a high yield.

3. A process for the preparation of a 5,5'-bi-1H-tetrazole diammonium salt according to claim 1, wherein the dicyan, sodium azide and ammonium chloride are fed at such a ratio that the molar ratio (B/A) of the sodium azide (B) to the ammonium chloride (A) is from 0.9 to 1.5, and the molar ratio (B/C) of the sodium azide (B) to the dicyan (C) is from 4.0 to 2.0.

4. A process for the preparation of a 5,5'-bi-1H-tetrazole diammonium salt according to claim 2, wherein after the dicyan is introduced, the reaction solution is reacted in two steps at a temperature of from 45 to 55° C. for from 0.5 to 2 hours and, then, at a temperature of from 85 to 95° C. for from 3 to 8 hours.

* * * * *